United States Patent [19]

Brandt et al.

[11] 4,361,902

[45] Nov. 30, 1982

[54] COLLIMATOR FOR X-RAY DIAGNOSTIC APPARATUS

[75] Inventors: Richard T. Brandt, New Berlin; Robert B. Hauck, Delafield, both of Wis.

[73] Assignee: General Electric Company, Milwaukee, Wis.

[21] Appl. No.: 166,483

[22] Filed: Jul. 7, 1980

[51] Int. Cl.³ .............................................. G03B 41/16
[52] U.S. Cl. ..................................... 378/152; 378/150
[58] Field of Search ........................ 250/511, 512, 513

[56] References Cited

U.S. PATENT DOCUMENTS

Re. 25,118  1/1962  Graves ................................. 250/511
3,187,179   6/1965  Craig .................................... 250/511

Primary Examiner—Craig E. Church
Attorney, Agent, or Firm—Robert C. Sullivan; Dana F. Bigelow; Douglas E. Stoner

[57] ABSTRACT

A collimator assembly for defining an aperture for the passage of a diagnostic x-ray beam in an x-ray diagnostic apparatus which may, for example, be used in computer assisted tomography. The collimator assembly comprises a framework adapted to be secured to the x-ray apparatus contiguous the x-ray tube, and includes a first and a second blade subassembly lying in a common plane with each other in the path of x-rays emanating from the x-ray tube. Leaf spring means connect each of the blade subassemblies to the framework, the leaf spring means biasing the first and second blade subassemblies into abutting relation to each other whereby to define a zero aperture condition for the passage of a diagnostic x-ray beam through said collimator assembly to the patient. Cam follower means are carried by each of the respective first and second blade subassemblies, and movable cam means are mounted on the framework and engageable with the cam follower means of said first and said second blade subassemblies whereby movement of the cam means is effective to move the first and second blade subassemblies against the biasing force of the spring means to a controlled degree of opening between the first and second blade subassemblies whereby to define a collimating aperture of a predetermined size between said subassemblies for the passage of a diagnostic x-ray beam of a predetermined size to the patient. A further feature of the collimator assembly is the use of a direct acting sensing arrangement for sensing the collimating opening between the two blade subassemblies. This sensing arrangement is embodied in an electromagnetic transducer in the form of a linear variable differential transformer.

9 Claims, 6 Drawing Figures

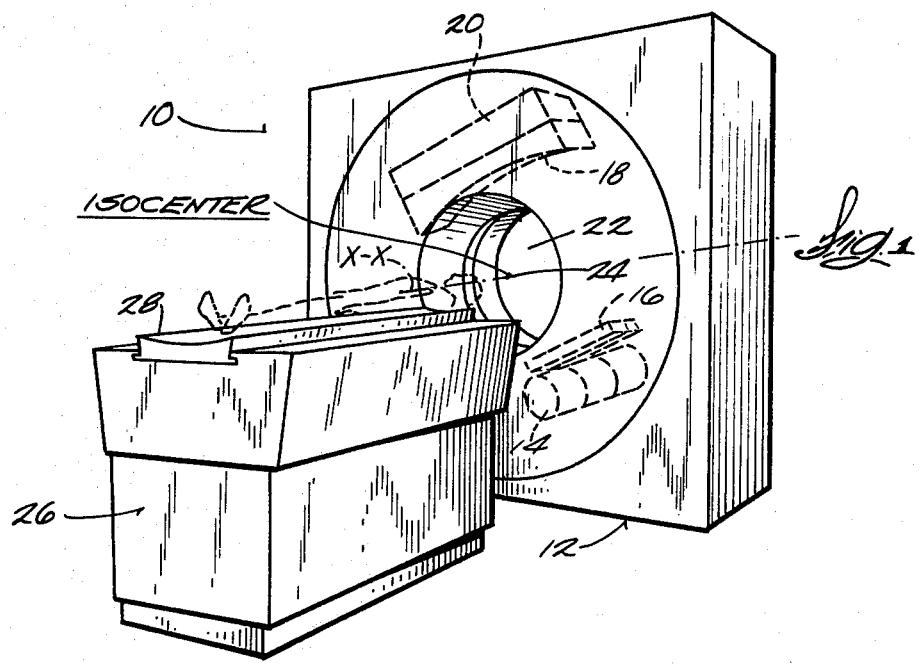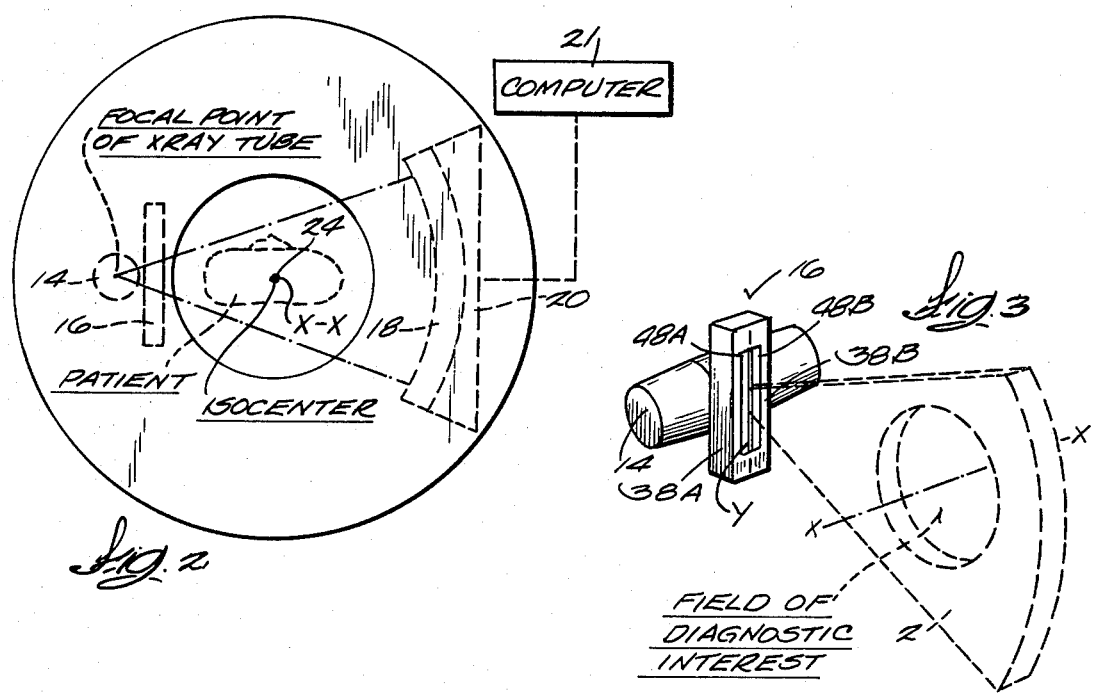

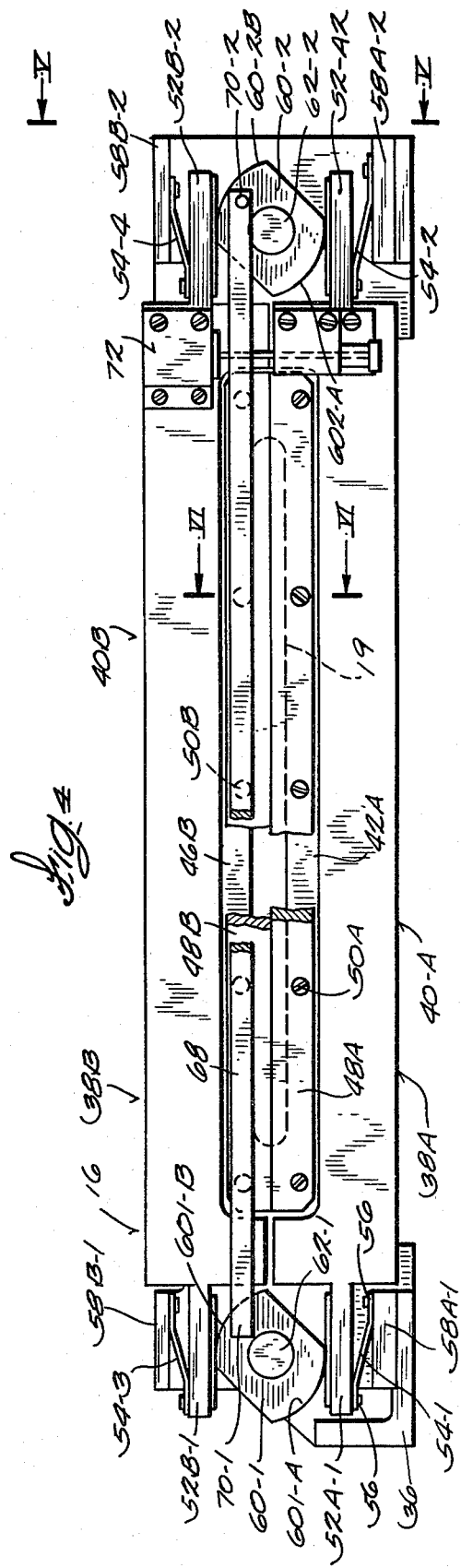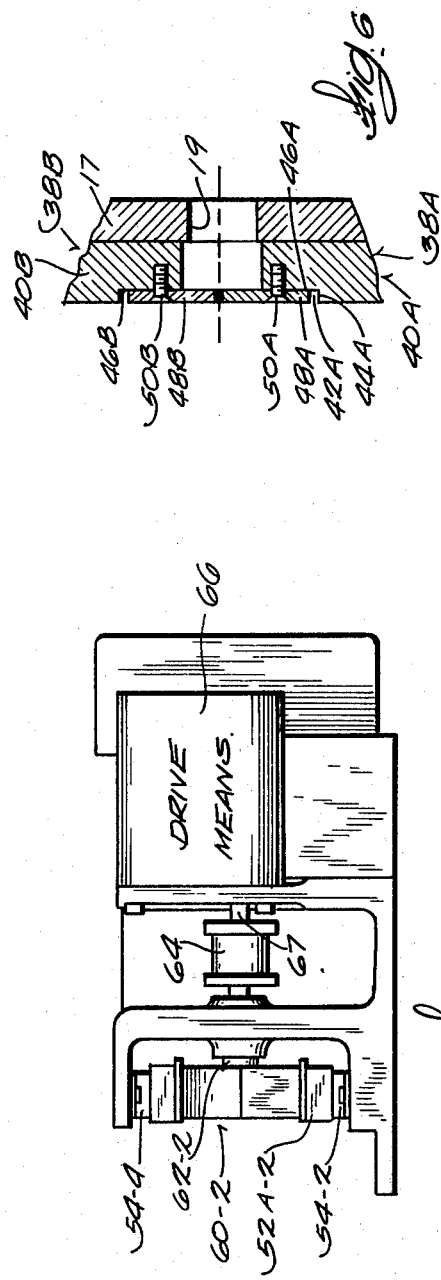

COLLIMATOR FOR X-RAY DIAGNOSTIC APPARATUS

TECHNICAL FIELD

This invention relates to x-ray diagnostic apparatus and to a collimator for defining an aperture which directs a diagnostic beam of x-rays in a predetermined manner toward the patient's body, and more particularly to a collimator which, while not restricted thereto, has particular utility in connection with computer assisted tomography.

BACKGROUND OF THE PRIOR ART

It has been known in the prior x-ray technology to move an x-ray tube circumferentially to successive angularly spaced points along an arc drawn from an isocenter which corresponds substantially to the center of the patient's body, transmitting a beam of x-rays toward the patient at each of the successive positions of the x-ray tube, and superimposing onto a common sheet of film a plurality of images resulting from the x-ray beams transmitted in the plurality of angularly spaced positions of the x-ray tube. The plurality of superimposed x-ray images obtained in this manner and superimposed upon each other on the same sheet of film results in a composite x-ray picture in which only one plane is in focus, namely, a plane passing through the isocenter. The technique just described is conventional x-ray tomography.

A more recent development in diagnostic x-ray technology has been the development of what is known as "computer assisted tomography." In x-ray diagnostic apparatus for use in computer assisted tomography, an x-ray tube, a collimator, a detector, and a data acquisition system are mounted for rotation as a unit interiorly of a gantry which houses the diagnostic imaging equipment. The gantry is provided with a hollow, centrally located, axially extending patient-receiving opening through which the patient may be moved linearly to predetermined desired positions relative to the x-ray apparatus. The x-ray tube and the collimator are mounted within the gantry on one side of the patient-receiving opening, and the detector and the data acquisition system are mounted within the gantry on an opposite side of the patient-receiving opening in diametrically opposed relation to the x-ray tube and collimator. The x-ray tube, collimator, and detector/data acquisition unit are all in fixed position relative to each other and define a diagnostic imaging assembly which rotates as a unit about the isocenter of the x-ray apparatus. As the diagnostic imaging assembly rotates through a single 360° rotation at a predetermined constant speed, a multiplicity of x-ray views, such as 288 or 576 views, for example, are taken at a corresponding number of angular positions of the imaging assembly. This multiplicity of views defines the data which is digitized and sent to a computer where an image is reconstructed electronically.

The following publication is cited as a source of further background information on computed tomography:

"Introduction to Computed Tomography"—General Electric Company, 1976.

It is also possible to use the x-ray apparatus shown and described herein, including the collimator assembly of the invention, in static (non-rotating) computer-assisted radiographic procedures in which the diagnostic imaging assembly (comprising the x-ray tube, the collimator, the detector, and the data acquisition system) is not rotating.

In an x-ray apparatus for use in computed tomography, in order to maximize the image quality obtained, it is desirable that the radial distance between the focal point of the x-ray tube and the isocenter of the x-ray apparatus be reduced to a minimum, and that the detector which lies diametrically opposite from the x-ray tube and from the collimator should be positioned as far as possible radially outwardly from the outer periphery of the patient-receiving opening while still being confined within the hollow interior of the gantry.

It has also been found desirable to increase the diameter of the patient-receiving opening in the gantry as compared to the size of the patient-receiving opening in the prior art tomographic x-ray apparatus.

With the gantry having a larger diameter patient-receiving opening than in the prior art and with the x-ray tube and detector moved to optimum radial positions in the gantry relative to the isocenter of the apparatus, the radial space available for the collimator, which defines the diagnostic beam aperture, is reduced considerably, with the result that the collimator of the type used in the prior art computed tomography apparatus is too large in a radial direction to be received in the space available when the x-ray tube and the diametrically opposite detector device are positioned in their optimum radial positions for greatest operational efficiency and for optimum image resolution.

STATEMENT OF THE INVENTION

Accordingly, it is an object of the present invention to provide a collimator assembly for use with x-ray diagnostic apparatus which is more compact than collimator apparatus of the prior art.

It is a further object of the invention to provide a collimator or diagnostic beam defining aperture assembly of compact construction which, while not necessarily restricted to such use, is particularly adapted for use with an x-ray diagnostic apparatus of the computed tomography type in which the compact structure of the collimator assembly permits optimum location of the x-ray tube and of the diametrically opposite detector device whereby to maximize operating efficiency and image resolution, and hence whereby to maximize the quality of the data transmitted to the associated computer for image reconstruction.

It is still a further object of the invention to provide a collimator assembly which, while not necessarily restricted thereto, is particularly adapted for use with an x-ray diagnostic apparatus of the computed tomography type, and in which the collimator assembly is so constructed that the movable collimator blade members which define the aperture for the diagnostic beam are so mounted as to be constantly maintained in a fixed plane which has a critical relationship to the geometry of the x-ray apparatus.

It is another object of the invention to provide a collimator assembly for defining the diagnostic beam aperture in an x-ray diagnostic apparatus in which the spacing between the collimator blades which define the diagnostic beam aperture is sensed by a direct measuring arrangement such as a linear variable differential transformer (LVDT) which directly senses the size of the opening between the aperture blades of the collimator assembly.

BRIEF SUMMARY OF THE INVENTION

In achievement of these objectives, there is provided in accordance with the invention a collimator assembly for defining an elongated aperture for the passage of a diagnostic x-ray beam in an x-ray diagnostic apparatus, said assembly comprising a framework adapted to be secured to the x-ray apparatus contiguous the x-ray tube, said assembly comprising a first and a second blade subassembly, each of said first and said second blade subassemblies respectively comprising a corresponding elongated aperture bounding means cooperating with and in confronting relation to the elongated aperture bounding means of the other of said blade subassemblies, said elongated aperture bounding means of said first and said second blade subassemblies lying in a common plane which is in the projected path of x-rays which the x-ray tube is adapted to emanate, spring means operatively associated with said subassemblies and with said framework, said spring means biasing said first and said second blade subassemblies to a position in which said elongated aperture bounding means of said respective subassemblies are in mutually abutting relation to define a zero aperture condition for the non-passage of a diagnostic x-ray beam through said collimator assembly to the patient, cam follower means carried by each of the respective first and second blade subassemblies, and movable cam means mounted on said framework and engageable with the cam follower means of said first and said second blade subassemblies to move said subassemblies against the biasing force of said spring means to provide a predetermined spacing between said elongated aperture bounding means of said first and said second subassemblies, and thus whereby to provide an elongated collimating aperture having a size determined by said spacing for passage of a diagnostic x-ray beam to the patient.

In accordance with a further feature of the invention, an electromagnetic transducer embodied in a linear variable differential transformer is provided and includes a first and a second element each respectively mounted on and movable with a corresponding one of the first and second blade subassemblies, whereby movement of said blade subassemblies relative to each other produces a signal which is representative of the relative movement of the two blade subassemblies.

BRIEF DESCRIPTION OF THE DRAWINGS

Further objects and advantages of the invention will become apparent from the following description taken in conjunction with the accompanying drawings in which:

FIG. 1 is a perspective view, partially diagrammatic, showing an x-ray diagnostic apparatus of the computed tomography type, and embodying an improved collimator assembly in accordance with the present invention;

FIG. 2 is a diagrammatic view taken transverse of the longitudinal axis of the apparatus of FIG. 1 showing the relative positions of the various components of the diagnostic imaging assembly, including the x-ray tube, the collimator, and the detector/data acquisition unit;

FIG. 3 is a perspective view, partially diagrammatic, showing the x-ray tube, the collimator, and the fan-shaped x-ray beam which emerges from the collimator, with the beam lying in a plane transverse of the longitudinal axis X—X of the gantry and of the patient-supporting table;

FIG. 4 is a view in elevation of the collimator assembly;

FIG. 5 is an end view of the assembly of FIG. 4 taken along line V—V of FIG. 4; and FIG. 6 is a view in section taken along line VI—VI of FIG. 4.

DESCRIPTION OF THE PREFERRED EMBODIMENT

Referring now to the drawings and more particularly to FIGS. 1, 2, and 3, there is shown an x-ray diagnostic apparatus generally indicated at 10 of the computed tomography type. The apparatus 10 comprises a gantry generally indicated at 12 which houses diagnostic imaging equipment, including an x-ray tube 14, a collimator assembly generally indicated at 16, a detector unit 18, and a data acquisition unit 20. The gantry is provided with a centrally located, axially extending patient-receiving opening 22. X-ray tube 14 and collimator assembly 16 are mounted on one side of the patient-receiving opening 22, and detector 18 and data acquisition unit 20 are mounted on the opposite side of patient-receiving opening 22 in diametrically opposed relation to x-ray tube 14 and collimator assembly 16. X-ray tube 14, collimator assembly 16, detector unit 18, and data acquisition unit 20 are all fixed with respect to each other and together define what will be referred to as the "diagnostic imaging subassembly." Means which form no part of the present invention is provided for rotating the diagnostic imaging subassembly within the interior of gantry 12 and about the central horizontal axis X—X of gantry 12 which passes through the isocenter 24 of the apparatus. A table generally indicated at 26 is provided as part of the x-ray diagnostic apparatus 10 and provides a support for the patient. Table 26 includes a patient support portion or "cradle" 28 which is movable relative to the main portion of table 26 to permit the patient to be moved into the patient-receiving opening 22 of gantry 12 in order to be properly positioned for the diagnostic procedure.

Referring now to FIG. 4, the collimator assembly generally indicated at 16, and which defines the aperture for the diagnostic beam, comprises a framework 36 which is suitably supported interiorly of gantry 12 in such manner that collimator assembly 16 is positioned in fixed relation to x-ray tube 14, detector 18, and data acquisition system 20.

Collimator assembly 16 includes a plate 17 which extends parallel to and in substantially abutting relation to the radially outer surface of blade subassemblies 38A and 38B (relative to axis X—X of FIGS. 1-3, inclusive). Plate 17 has an elongated aperture 19 therein (FIGS. 4 and 6) through which the x-ray beams pass. The adjustably movable collimating blades 48A and 48B (to be described) which form part of collimator assembly 16 lie radially inwardly of aperture 19 (relative to axis X—X in FIGS. 1-3, inclusive), in overlying masking relation to aperture 19, with the spacing between collimating blades 48A and 48B being adjustable to control the axial thickness (relative to axis X—X in FIGS. 1-3, inclusive), of the x-ray beam which is directed toward the patient.

Collimator assembly 16 includes two blade subassemblies respectively generally indicated at 38A and 38B which are floatably mounted relative to collimator frame member 36 by leaf springs generally indicated at 54 and specifically indicated at 54-1, 54-2, 54-3, and 54-4. Leaf springs 54 bias blade subassemblies 38A and 38B and collimating blades 48A and 48B carried by the respective blade subassemblies toward a closed (zero aperture) position. Leaf springs 54 are made of a suitable material such as 1095 pretempered spring steel having a thickness of 20 mils.

One end of each of the leaf springs 54 is fastened by screws 56 to a corresponding spring support pad 58 which forms part of the collimator frame structure 36, while the opposite end of each of the leaf springs 54 is fastened by other screws 56 to a corresponding extension 52 of one of the bladeholders 40A or 40B. When the bladeholders 40A, 40B move relative to each other under the influence of cams 60-1, 60-2, as will be described, each of the respective leaf springs 54, although anchored to the collimator frame structure 36 by screw 56, nevertheless moves in a pivotal fashion about its connection to the frame structure. All of the leaf springs 54 move in arcs of equal radius about their respective connections to the collimator frame structure.

The two blade subassemblies 38A and 38B may be moved relative to each other to define the diagnostic beam aperture as will be explained hereinafter. The two blade subassemblies 38A and 38B are of similar construction.

Blade subassembly 38A includes a bladeholder or blade support member generally indicated at 40A which is recessed for a substantial portion of its length as indicated at 42A, recess 42A being bounded by a ledge 44A and by a wall portion 46A (FIG. 6). The elongated recess 42A is adapted to receive collimating blade 48A which is secured to bladeholder 40A by screws 50A which pass through collimating blade 48A and into the wall portion 46A whereby to detachably secure collimating blade 48A to bladeholder 40A. At the opposite ends thereof, bladeholder 40A is provided with legs or extensions 52A-1 and 52A-2 which define cam follower portions adapted to cooperate with the operating cam members 60-1 and 60-2 and with the leaf spring mounting arrangements for the blade subassembly as will be described hereinafter.

In a similar manner, blade subassembly 38B comprises a bladeholder 40B of construction similar to bladeholder 40A previously described and which supports collimating blade member 48B which is secured by screws 50B to recessed wall 46B of bladeholder 40B in the same manner as described in connection with blade subassembly 38A. The opposite ends of bladeholder 40B are provided with extensions or legs 52B-1 and 52B-2 which define cam follower portions adapted to cooperate with cam members 60-1 and 60-2 and with the leaf spring mounting arrangements in the same manner as blade subassembly 38A. Bladeholders 40A and 40B are made of a suitable material such as aluminum, and the collimating blades 48A and 48B are made of sintered tungsten.

Bladeholder 40A is floatingly mounted with respect to support frame member 36 by a pair of leaf spring members 54-1 and 54-2 (FIG. 4) at the opposite ends of the collimator assembly. Spring 54-1 is anchored at its right-hand end relative to the view of FIG. 4 to a spring support pad 58A-1 which is part of stationary framework 36 of the collimator assembly; and spring 54-1 is anchored at its left-hand end relative to FIG. 4 to the outer (i.e., left-hand in FIG. 4) end of the surface of extension 52A-1 which is in facing relation to spring support pad 58A-1. Spring 54-2 at the opposite end of bladeholder 40A is anchored at its right-hand end (as viewed in FIG. 4) to spring support pad 58A-2 which forms part of stationary frame structure 36; and spring 54-2 is anchored at its opposite or left-hand end (as viewed in FIG. 4) to the inner or left-hand end of the surface of extension 52A-2 of bladeholder 40A (as viewed in FIG. 4) which is in facing relation to spring support pad 58A-2.

In a similar manner, bladeholder 40B is spring mounted relative to the stationary frame structure 36 by means of leaf springs 54-3 and 54-4 at the opposite ends of the collimator assembly. Spring 54-3 is anchored at one end to the free end of extension 52B-1 of bladeholder 40B, and at its opposite end to the surface of spring support pad 58B-1 which is in facing relation to extension 52B-1. Spring support pad 58B-1 forms part of frame structure 36. Leaf spring 54-4 at the opposite end of the collimator assembly is anchored at one end to the inner end (opposite the free end) of extension 52B-2 of blade support member 40B. The opposite end of leaf spring 54-4 is connected to the surface of spring support pad 58B-2 which is in facing relation to extension 52B-2. Spring support pad 58B-2 forms part of frame structure 36.

Leaf springs 54 serve to bias the two bladeholders 40A and 40B and hence the collimating blades 48A and 48B supported thereby toward an abutting relation to each other as seen in the view of FIG. 4 in which the two blades 48A and 48B are in closed position with respect to each other (assuming cams 60-1 and 60-2 are in the limit position shown in FIG. 4), whereby to prevent the egress through collimating blades 48A and 48B of any x-rays from passage 19 in plate 17 of collimator assembly 16.

In order to control the spacing between the two collimating blades 48A and 48B and thus to control the size of the beam-defining aperture between the two blades, a pair of cam members generally indicated at 60-1 and 60-2 are mounted for angular rotation at the opposite ends of the collimator assembly. Cam 60-1 at the left-hand end of the view of FIG. 4 is positioned between the extensions or legs 52A-1 and 52B-1 of the respective bladeholders 40A and 40B, and is mounted on camshaft 62-1. Cam 60-2 at the opposite or right-hand end of the collimator assembly as viewed in FIG. 4 is positioned between extensions 52A-2 and 52B-2 of the respective bladeholders 40A and 40B. Springs 54 constantly maintain extensions 52A-1, 52A-2, and 52B-1, 52B-2 of the respective bladeholders 40A and 40B in intimate contact with the faces of the two cams 60-1 and 60-2.

Cam 60-2 is mounted on a camshaft 62-2 which is connected through a coupling 64 to the output shaft 67 of a drive means 66 (FIG. 5) which includes an electric motor and a gear drive train driven by the electric motor and which reduces the speed at the output shaft 67 of drive means 66, and thus at camshaft 62-2, to some low value such as 1 r.p.m. The electric motor of drive means 66 is preferably of the permanent magnet reversible AC type which prevents coasting of the output shaft 67 and of the connected camshaft 62-2 when the electric drive motor is de-energized.

The electric motor of drive means 66 may be, for example, a 20-pole, 60 hertz, permanent magnet alternating current synchronous reversible instrument motor, of the type manufactured by Hurst Manufacturing Corporation, Princeton, Ind. 47670, under the designation Model T. The motor just described has a shaft speed of 360 revolutions per minute. The associated gear box or gear train to which the shaft of the motor is connected has a reduction ratio of 360:1, for example, whereby the speed of gear box output shaft 67 is one revolution per minute, to thereby rotate cam shaft 62-2 at the same speed, namely, one revolution per minute.

The reduction gear train which is interposed between the electric motor and output shaft 67 of drive means 66 serves as a brake which prevents unintended reverse movement of collimator blades 48A, 48B when the electric motor of drive means 66 is de-energized, thereby maintaining collimator blades 48A, 48B in a given adjusted position as determined by the linear variable differential transformer 72 (to be described) and the associated control circuit.

Each of cams 60-1 and 60-2 has a pair of diametrically opposite variable radius, elliptical contour cam surfaces 60-1A, 60-1B (cam 60-1) and 60-2A, 60-2B (cam 60-2). Cam surfaces 60-1A and 60-2A of the respective cams 60-1 and 60-2 are respectively adapted to cammingly engage the extensions 52A-1 and 52A-2 of bladeholder 40A; whereas cam surfaces 60-1B and 60-2B of the respective cams 60-1 and 60-2 are adapted to cammingly engage the extensions 52B-1 and 52B-2 at the opposite ends of bladeholder 40B.

The two cams 60-1 and 60-2 are linked together by a connecting link 68 which is pivotally connected at its opposite ends at pivot points 70-1 and 70-2 to the respective cam members 60-1 and 60-2.

A further important feature of the collimator assembly is the use of an electromagnetic transducer in the form of a linear variable differential transformer (LVDT) indicated at 72 which is mounted as part of the collimator assembly and is used to sense the size of the opening between the collimating blades 48A and 48B.

The linear variable differential transformer (LVDT) 72 is essentially an electromagnetic transducer in which one element thereof, such as an inductive winding, is mounted on one of the movable blade subassemblies, while the other element thereof, such as a ferromagnetic plunger or the like, is mounted on the other of the movable blade subassemblies. Movement of the two blade subassemblies 38A and 38B relative to each other to change the collimating aperture defined by blades 48A and 48B causes a movement of the elements of the linear variable differential transformer relative to each other and transmits a signal to an appropriate control circuit (not shown) which controls drive motor 66 for cams 60-1 and 60-2. The control circuitry for the linear variable differential transformer (LVDT) 72 can be set to provide any desired number of precise aperture settings.

Linear variable differential transformers per se are well known in the art and are commercially available. For example, a linear variable differential transformer is manufactured by Trans-Tex, Route No. 83, Ellington, Conn. 06209, and is identified as part #241-000.

In the position shown in the drawings, the collimator blades 48A and 48B are in fully closed position, and the two synchronized elliptical cams 60-1 and 60-2 are in their limit position. To open collimator blades 48A and 48B relative to each other to provide a diagnostic beam-defining aperture between the two collimating blades, drive means 66 is energized to rotate cam 60-2 in a counterclockwise direction relative to FIG. 4. Any angular motion imparted to cam 60-2 causes a corresponding motion of cam 60-1 due to the connecting link 68 between the two cams 60-1 and 60-2. Cams 60-1 and 60-2 rotate in a counterclockwise direction relative to the view shown in FIG. 4 to cause the two bladeholders 40A and 40B to move apart, carrying with them collimating blades 48A and 48B. When linear variable differential transformer (LVDT) 72 senses that collimating blades 48A and 48B have moved apart a predetermined distance corresponding to one of the calibrated settings of the control circuit for cam drive means 66, the electric motor of drive means 66 is de-energized to stop further rotation of cams 60-1 and 60-2. The permanent magnet AC electric motor which forms part of drive means 66 has the characteristic that upon being de-energized, it will stop immediately without coasting. Also, the reduction gear train which is interposed between the electric motor and output shaft 67 of drive means 66 serves as a brake which prevents unintended reverse movement of collimator blades 48A, 48B when the electric motor of drive means 66 is de-energized to thereby maintain collimator blades 48A, 48B in a given adjusted position. To move collimator blades from an open position toward a closed position, drive means 66 is reversed as compared to its direction for opening movement and rotates cams 60-1 and 60-2 in a clockwise direction relative to FIG. 4, which cams 60-1 and 60-2 and collimator blades 48A and 48B having a limiting position in the closing direction as seen in FIG. 4. Springs 54 cause collimator blades 48A, 48B to move toward closed position as cams 60-1 and 60-2 approach the position shown in FIG. 4.

It should be noted that when cams 60-1 and 60-2 are rotated to move collimator blades 48A and 48B apart from the closed position shown in FIG. 4, the mounting of all the leaf springs 54 is such that all of the leaf springs 54 move in arcuate paths of equal radius about their respective connections to the stationary frame structure 36, to thereby cause a slight equal linear movement of each of the collimating blade subassemblies 38A and 38B to the left relative to the view shown in FIG. 4. Upon closing, blade subassemblies 38A and 38B move equal distances to the right relative to the view of FIG. 4.

Since both of the blade subassemblies 38A and 38B move equal distances in the same direction as each other upon either opening or closing movement, the linear variable differential transformer (LVDT), which has one part thereof mounted on one blade subassembly 38A and the other part thereof mounted on the other blade subassembly 38B, is not affected adversely in any manner since the respective portions of the LVDT mounted on the separate respective blade subassemblies always both move together equal distances in the same direction. The mounting arrangement of leaf springs 54 with respect to the blade subassemblies 38A and 38B and with respect to the frame structure of the collimator assembly so as to cause movement of the respective blade subassemblies 38A and 38B equal distances in the same linear direction permits the use of a direct-acting sensing device such as the LVDT for the purpose of sensing the spacing between collimator blades 48A and 48B. On the other hand, if the various springs 54 were pivotally mounted in such manner that the two blade subassemblies 38A and 38B moved in opposite directions when acted upon by cams 60-1 and 60-2, it would be necessary to use an indirect measuring arrangement for sensing the spacing of the collimator blades which would be less satisfactory than the direct measurement provided by the linear variable differential transformer (LVDT).

It should also be noted that the use of leaf springs 54 for the spring mounting of collimator blade subassemblies 38A and 38B serves to substantially prevent any lateral displacement of bladeholders 40A and 40B and of collimator blades 48A and 48B with respect to each other, and to insure that collimator blades 48A and 48B are constantly maintained in a predetermined fixed plane having a predetermined desired relationship to the geometry of x-ray apparatus 10.

The collimator assembly 16 is mounted in the interior of gantry 12 (FIG. 1) in such manner that the slot or beam-defining aperture Y defined between and bounded by the elongated collimator blades 48A and 48B is so oriented, as best seen in FIG. 3, that the fan-shaped x-ray beam Z which emerges from the slot Y lies in a plane transverse of the longitudinal axis X—X of gantry 12 and of patient-supporting table portion 28. The space between the facing edges of collimator blades 48A and 48B extends parallel to axis X—X and defines the "thickness" of x-ray beam Z in the direction X—X which extends axially of gantry 12 and of table portion 28.

The thickness of x-ray beam Z (FIG. 3) defines the thickness of the "slice" of the patient's body in a plane transverse of longitudinal axis X—X which is subjected to the x-rays during the 360° scan and also during static (non-rotating) radiographic procedures in which the diagnostic imaging assembly is not rotating.

In the rotating computed tomography radiographic procedure, and with the patient in a predetermined desired position within patient-receiving opening 22 of gantry 12, the diagnostic imaging assembly comprising the x-ray tube 14, collimator assembly 16, detector 18, and data acquisition system 20 is rotated at constant speed through 360° as a unit about the longitudinal axis X—X of x-ray apparatus 10. During the 360° rotation of the diagnostic imaging assembly, a multiplicity of x-ray views, such as 288 or 576 views, for example, are taken at a corresponding number of angular positions of the imaging assembly. This multiplicity of views is digitized and sent to a computer 21 which may be remotely located relative to gantry 12. The computer 21 reconstructs the diagnostic image electronically.

The "cradle" table portion 28 of table 26 may be moved axially along axis X—X (FIGS. 1 and 3) to change the position of the patient relative to gantry 12 and to the diagnostic imaging equipment which is rotatably mounted in gantry 12, whereby to permit scanning of the patient's body in different planes transverse of the patient's body. The patient is supported on the movable "cradle" table portion 28 within the patient-receiving opening 22 of gantry 12 in a similar manner for both the computed tomography procedure in which the diagnostic imaging equipment is rotatably movable, and in the static (non-rotating) radiographic procedures.

From the foregoing detailed description of the invention, it has been shown how the objects of the invention have been obtained in a preferred manner. However, modifications and equivalents of the disclosed concepts such as readily occur to those skilled in the art are intended to be included within the scope of the invention.

The embodiments of the invention in which an exclusive property or privilege is claimed are defined as follows:

1. A collimator assembly for defining an elongated aperture for the passage of a diagnostic x-ray beam in an x-ray diagnostic apparatus, said assembly comprising a framework, said assembly comprising a first and a second blade subassembly mounted on said framework, each of said first and said second blade subassemblies respectively comprising a corresponding elongated aperture bounding means cooperating with and in confronting relation to the elongated aperture bounding means of the other of said blade subassemblies, said elongated aperture bounding means of said first and said second blade subassemblies lying in a common plane which is in the projected path of x-rays which the x-ray tube is adapted to emanate, spring means operatively associated with said subassemblies and with said framework, said spring means biasing said first and said second blade subassemblies to a position in which said elongated aperture bounding means of said respective subassemblies are in mutually abutting relation to define a zero aperture condition for the non-passage of a diagnostic x-ray beam through said collimator assembly to the patient, each of said blade subassemblies comprising a first and a second cam follower means at the respective opposite ends thereof, said assembly comprising a first cam means mounted on said framework and interposed between the respective first cam follower means of both of said blade subassemblies and contiguous one end of said blade subassemblies, and a second cam means mounted on said framework and interposed between the respective second cam follower means of both of said blade subassemblies and at the opposite end of said blade subassemblies, link means connecting said first and said second cam means to each other such that movement of one of said cam means is imparted to the other of said cam means, means for driving one of said cam means such that both said first and said second cam means move to cause movement of said first and said second blade subassemblies relative to each other against the biasing force of said spring means to provide a predetermined spacing between said elongated aperture bounding means of said first and said second subassemblies, and means for securing said collimator assembly to said x-ray diagnostic apparatus.

2. A collimator assembly as defined in claim 1 in which said spring means maintains said cam follower means in constant contact with said cam means.

3. A collimator assembly as defined in claim 1 in which the direction of opening and closing movement of said blade subassemblies is in a direction normal to the longitudinal axis of said blade subassemblies, and in which said spring means comprises separate spring means associated with each of said respective subassemblies and with said framework, each of said separate spring means comprising a leaf spring having one end thereof connected to the corresponding blade subassembly and the opposite end thereof connected to said framework, the respective leaf springs being so dimensioned and so mounted that opening or closing movement of said blade subassemblies causes all of the respective leaf springs to move pivotally in arcs of equal radius about their respective connections to said framework, with consequent linear movement of the respective blade subassemblies in a direction parallel to said longitudinal axis, said leaf springs being mounted to cause both blade subassemblies to move equal linear distances and in the same direction as each other upon either opening or closing movement of said blade subassemblies.

4. A collimator assembly as defined in claim 1 in which each of said blade subassemblies comprises a bladeholder and a collimating blade secured to the respective bladeholder, said collimating blade defining said elongated aperture bounding means, and in which said spring means biases the respective collimating blades of said first and second blade subassemblies into abutting relation to each other whereby to define said zero aperture condition.

5. A collimator assembly as defined in claim 1 in which said spring means is a leaf spring means.

6. A collimator assembly as defined in claim 1 in which said cam means is rotatable, and in which said collimator assembly comprises drive means for rotating said cam means.

7. A collimator assembly as defined in claim 6 in which said drive means comprises an electric motor and reduction gear means interposed between said electric motor and said cam means whereby to rotate said cam means at a substantially lower rate of speed than the rate of rotation of said electric motor.

8. A collimator assembly for defining an elongated aperture for the passage of a diagnostic x-ray beam in an x-ray diagnostic apparatus, said assembly comprising a framework, said assembly comprising a first and a second blade subassembly mounted on said framework, each of said first and said second blade subassemblies respectively comprising a corresponding elongated aperture bounding means cooperating with and in confronting relation to the elongated aperture bounding means of the other of said blade subassemblies, said elongated aperture bounding means of said first and said second blade subassemblies lying in a common plane which is in the projected path of x-rays which the x-ray tube is adapted to emanate, spring means operatively associated with said subassemblies and with said framework, said spring means biasing said first and said second blade subassemblies to a position in which said elongated aperture bounding means of said respective subassemblies are in mutually abutting relation to define a zero aperture condition for the non-passage of a diagnostic x-ray beam through said collimator assembly to the patient, each of said blade subassemblies comprising a first and a second cam follower means at the respective opposite ends thereof, said collimator assembly comprising a first cam means mounted on said framework and interposed between the respective first cam follower means of both of said blade subassemblies and contiguous one end of said blade subassemblies, and a second cam means mounted on said framework and interposed between the respective second cam follower means of both of said blade subassemblies and at the opposite end of said blade subassemblies, link means connecting said first and said second cam means to each other such that movement of one of said cam means is imparted to the other of said cam means, means for driving one of said cam means such that both said first and said second cam means move to cause movement of said first and second blade subassemblies relative to each other against the biasing force of said spring means to provide said predetermined spacing between said subassemblies, sensing means for sensing the size of the beam-defining aperture between said elongated aperture bounding means of said first and said second blade subassemblies, said sensing means comprising an electromagnetic transducer, said electromagnetic transducer comprising a first element mounted on and movable with one of said blade subassemblies, and a second element mounted on and movable with the other of said blade subassemblies, such that movement of said two blade subassemblies relative to each other produces a corresponding movement of said first and second elements relative to each other to produce a signal which is indicative of said relative movement of said two blade subassemblies, and means for securing said collimator assembly to an x-ray diagnostic apparatus.

9. A collimator assembly for defining an elongated aperture for the passage of a diagnostic x-ray beam in an x-ray diagnostic apparatus, said assembly comprising a framework, said assembly comprising a first and a second blade subassembly mounted on said framework, each of said first and said second blade subassemblies respectively comprising a bladeholder and an elongated collimating blade secured to the respective bladeholder, the respective collimating blades of said first and said second blade subassemblies lying in a common plane which is in the projected path of x-rays which the x-ray tube is adapted to emanate, separate leaf spring means operatively associated with each of said subassemblies and with said framework, said separate leaf spring means biasing said first and said second blade subassemblies to a position in which the collimating blades of said respective subassemblies are in mutually abutting relation to define a zero aperture condition for the non-passage of a diagnostic x-ray beam through said collimator assembly to the patient, each of said blade subassemblies comprising first and a second cam follower means at the respective opposite ends thereof, said collimator assembly comprising a first cam means mounted on said framework and interposed between the respective first cam follower means of both of said blade subassemblies and contiguous one end of said blade subassemblies, and a second cam means mounted on said framework and interposed between the respective second cam follower means of both of said blade subassemblies and at the opposite end of said blade subassemblies, link means connecting said first and said second cam means to each other such that movement of one of said cam means is imparted to the other of said cam means, means for driving one of said cam means such that both said first and said second cam means move to cause movement of said first and second blade subassemblies relative to each other against the biasing force of spring means to provide said predetermined spacing between said subassemblies, a linear variable differential transformer sensing means for sensing the size of the beam-defining aperture between said collimating blades of said first and said second blade subassemblies, said linear variable differential transformer comprising a first element mounted on and movable with one of said blade subassemblies, and a second element mounted on and movable with the other of said blade subassemblies, such that movement of said two blade subassemblies relative to each other produces a corresponding movement of said first and second elements relative to each other to produce a signal which is indicative of said relative movement of said two blade subassemblies, and means for securing said collimator assembly to an x-ray diagnostic apparatus.

* * * * *